(12) United States Patent
Zhang et al.

(10) Patent No.: US 7,113,896 B2
(45) Date of Patent: Sep. 26, 2006

(54) SYSTEM AND METHODS FOR PROCESSING BIOLOGICAL EXPRESSION DATA

(76) Inventors: Zhen Zhang, 14104 Big Branch Dr., Dayton, MD (US) 21036; Hong Zhang, 22 Black Hawk Trail, Savannah, GA (US) 31411

( * ) Notice: Subject to any disclaimer, the term of this patent is extended or adjusted under 35 U.S.C. 154(b) by 735 days.

(21) Appl. No.: 10/144,455

(22) Filed: May 13, 2002

(65) Prior Publication Data
US 2003/0055615 A1 Mar. 20, 2003

Related U.S. Application Data

(60) Provisional application No. 60/290,526, filed on May 11, 2001.

(51) Int. Cl.
*G06F 17/10* (2006.01)
(52) U.S. Cl. .............................................. 703/2; 705/7
(58) Field of Classification Search .................. 703/2; 706/19; 705/7
See application file for complete search history.

(56) References Cited

U.S. PATENT DOCUMENTS 5,281,840 A * 1/1994 Sarma .......................... 257/351
5,311,426 A * 5/1994 Donohue et al. ........... 422/102
6,810,368 B1 * 10/2004 Pednault ........................ 703/2

OTHER PUBLICATIONS

Systems Engineering Tools by Harold Chestnut, John Wiley & Sons, 1965, pp. 462 to 467.*

* cited by examiner

*Primary Examiner*—Albert W. Paladini
(74) *Attorney, Agent, or Firm*—Merchant & Gould

(57) ABSTRACT

A system and method for processing information in a data set that contains samples of at least two classes using an empirical risk minimization model, wherein each sample in the data set has an importance score. In one embodiment, the method includes the step of selecting samples of a first class being labeled with class label +1 and a second class with class label −1, from the data set, prescribing an empirical risk minimization model using the selected samples with an objective function and a plurality of constraints which adequately describes the solution of a classifier to separate the selected samples into the first class and the second class, modifying the empirical risk minimization model to include terms that individually limit the influence of each sample relative to its importance score in the solution of the empirical risk minimization model, and solving the modified empirical risk minimization model to obtain the corresponding classifier to separate the samples into the first class and the second class.

47 Claims, 8 Drawing Sheets ranks scores

FIG. 2

First 500 ORFs after clustering

Second 500 ORFs after clustering

Third 500 ORFs after clustering

Last 500 ORFs (#1968-#2467) after clustering (A)

(B)

SYSTEM AND METHODS FOR PROCESSING BIOLOGICAL EXPRESSION DATA

CROSS-REFERENCE TO RELATED APPLICATION

This application claims priority to U.S. Provisional Application Ser. No. 60/290,526, which was filed on May 11, 2001, in the United States Patent and Trademark Office and incorporated herein in its entirety by reference.

BACKGROUND OF THE INVENTION

1. Field of the Invention

The present invention generally relates to a system and methods for processing biological entities whose expression levels individually or collectively as patterns differentiate biological samples of different phenotypes associated with the presence of absence or severity of conditions or perturbations. More particularly, the present invention relates to a system and methods for processing including detecting and analyzing the collective patterns in biological expression levels for the purposes of selecting variables and deriving multivariate models to predict phenotypic differences in future data.

2. Description of the Related Art

The human genome project and the newly expanded effort into large scale gene expression profiling and protein profiling have generated an unprecedented large amount of data. Commercial companies, government agencies, and academic institutions have over the years invested heavily in the area of bioinformatics to develop infrastructures and technologies for the storage and compilation of data and to provide easy access to the constructed databases. However, in order to actually reap benefits from such amassed data for both scientific and commercial purposes, new and better analytical and computational tools are critically needed to allow researchers and scientists to extract relevant information from the vast amount of data and convert it into forms that are readily usable in academical and commercial research and development activities.

There are two basic approaches to the utilization of information from data: (1) the first principle approach in which current understandings and knowledge of physical laws are used to assemble piece of data and information together to form new knowledge and understandings that explain observed data; and (2) the pattern recognition approach in which regularities and associations among variables in observed data are identified to establish mathematical models that predict future data. These two approaches are closely related and can mutually benefit from each other. Explanations of observed data serve as the scientific foundations for pattern recognition based data modeling and prediction while trends and relationships in data detected through pattern recognition offer directions and generate hypotheses for further research.

Compared to our newly acquired ability to generate exponentially growing volumes of data, our knowledge and understandings in biomedical sciences are very limited, even with the extremely impressive progress we have made over the past decade. For the foreseeable future, pattern recognition based approach may continue to play an important role in the analysis of biomedical data. For commercial product development, such an approach may allow us to bypass some of the current unknowns and instead to establish direct linkage between extracted information from data and an endpoint of interest, such as diagnostic or therapeutics targets.

The development of high density arrays of oligonucleotides or complementary DNAs (microarrays) has made it possible to simultaneously analyze the expression levels of tens of thousands of genes in a single array (experiment). An overview of the current state of art of the technology may be found in (Eisen and Brown, 1998) and (Lockhart and Winzeler, 2000). The abundance of mRNA, measured through optical imaging and numerical post-processing procedures, can be eventually quantitatively represented as a vector of numerical values.

Recent advances in protein arrays and biochips have greatly facilitated protein functional analysis and expression profiling. Such high throughput devices, depending on the protein capturing approaches, measure the abundances of either a pre-selected set of proteins or a large number of unspecified proteins sharing certain common properties so that they are captured together. One of the most common methods of measuring protein abundance is mass spectrometry (MS). The intensity of individual peaks in the mass spectra represents the relative abundances of the corresponding proteins (including fragment of proteins) and peptides. The time-of-fly (TOF) measurements associated with the peaks indicate their molecular weights. Data from such devices, after normalization and calibration and appropriate preprocessing procedures, may also be represented as a vector of numeric values in which each entry is the relative abundance of a particular protein (or protein fragment/peptide) that is either known with its name or labeled by its mass weight.

Expression data are typically characterized by the very large number of measurements (tens of thousands genes in genomic expression data and hundreds or thousands proteins for proteomic expression data) in comparison to the relatively small number of data points (number of experiments).

To extract useful information from such expression data, various analytical and data visualization techniques have been proposed. These techniques center around three aspects of expression data analysis: 1) detection of expression patterns; 2) dimension reduction; and 3) data visualization. Algorithms based on cluster analysis have been used in many reported studies on gene expression profile analyses using microarray data (Eisen et. al., 1998). With a predefined similarity or distance measure, these algorithms reorganize the expression data in such a way that genes sharing similar expression profiles across multiple experiments are arranged together for easy identification of patterns. In a similar fashion, individual experiments with similar expression profiles over the entire set of genes may also be clustered together. For similar purposes, other techniques, such as self-organizing maps, have also been proposed to partition gene expression data into groups of genes and arrays of similar characteristics. The main advantage of these approaches is that it provides a holistic view of expression patterns across the entire set of observations. A noticeable drawback of such approaches is, however, that the majority of genes in the dataset, including those with strong expression variation patterns, might not be associated at all with a particular end point of interest (e.g., different phenotypes or experiment conditions). Consequently, expression patterns that are truly associated with the end point would have to have a strong presence in terms of the number of genes of similar profiles so that they could be detected among the large number of non-contributing expression patterns.

Singular value decomposition has recently been suggested to project expression data onto the so-called eigengene×eigenarray space to reduce dimensionality for better data interpretation (Alter et. al., 2000). The approach is similar to principal component analysis (PCA) in which the major eigengenes correspond to the directions represented by genes with the largest variance in their expression levels. Again, a similar drawback of this method is that those genes with the largest variance in their expression levels might not necessarily be associated with the end point of interest in the analysis.

Effective tools for expression data visualization allow human expert to interactively inspect the data and results during or after various analysis procedures, such as cluster structure from cluster analysis, and projection of individual experiments (arrays) onto a 2 or 3 dimensional space of selected eigenvectors after PCA.

In many expression data studies, one often has a specific endpoint of interest in mind, which could be the desired separation of specimens from subjects of different phenotypes (e.g., normal vs. tumor tissues) or the same type of specimens under different experiment conditions (e.g., yeast cells in normal cell division cycles vs. yeast cells under heat shock stress). For such cases, the purpose is to identify the variables (e.g., genes or proteins) whose expression variation patterns are associated with the different values or conditions of the endpoint of interest.

The identification of differentially expressed genes or proteins typically requires a set of expression data as training data in which the identity (label) of each experiment sample is known before hand. An analytical method that works under such an assumption is commonly referred to as a supervised method. One of the ways to identify differentially expressed genes or proteins is first to use a supervised method to derive a classification model (classifier) that assigns the experiments to a predefined number of known classes with minimum error. The contributions of individual variables to the classification model are then analyzed as a measurement of significance of the genes or proteins whose expression levels collectively as co-regulated patterns differentiate the different classes of experiments.

There are two fundamentally different approaches to the derivation of classification models. With the traditional statistical approach, the training data are used to estimate the conditional distributions for each of the classes of experiments. Based on the Bayes decision rule, a final classifier is then determined. A simple example of this approach is the Linear Discriminant Analysis (LDA) method (Fisher 1923). In LDA, the training data from two predefined classes are used to estimate the two class means and a pooled covariance matrix. The means and covariance matrix are then used in determine the classification model. It can be shown using the Bayes' decision rule that if the data are conditionally normally distributed and share the same covariance structure, LDA is the optimal classification models for separating the two classes of data.

The other approach to the derivation of classification models is called empirical risk minimization. In this approach, the model is determined directly by minimizing a predefined empirical risk function that is linked to the classification error of the model over the training data. The Support vector machine (SVM) (Vapnik, 1998) is one such method. In SVM, in addition to the minimization of empirical risk, it has also control over the complexity of the model to partially overcome the problem of over-fitting the training data.

The two approaches work differently and one could be more appropriate than the other for certain problems and vice versa for others. In general, the two approaches all produce good results for problems with a sufficiently large training data set. However, for problems with a very small training data set, both approaches are constrained in their way of utilizing the information contained in the limited number of samples.

In the traditional statistical approach, training data, whether they are located close to the boundaries between pairs of classes or far away from the boundaries, contribute equally to the estimation of the conditional distributions from which the final classification model is determined. Since the purpose of classification is to recover accurately the actual boundaries that separate the classes of data, training samples close to the separating boundaries should play a more important role than those samples that are far away. Using clinical diagnostic problems as an example, specimens from patients whose are borderline cases such as early stage diseases and benign cases should be more useful in defining precisely the disease and non-disease classes than those from patients with late stage diseases or young healthy controls.

Using the empirical risk minimization approach, on the other hand, the final classification model is largely determined based on the training data that are close to the class boundaries. The solution from SVM, for example, is determined exclusively by a subset of the training samples located along the class boundaries (support vectors). The overall data distribution information, as partially represented by the total available training samples, is ignored.

For problems with a sufficiently large number of training samples, asymptotically, both approaches will work well. A large set of training samples will allow for the precisely estimation of the conditional distributions including along the side that different classes separate from one another so that classifiers based on Bayes' decision rule will perform optimally; the empirical risk minimization approach will also be able to define a precise classification model based on training samples that representatively covers the spaces along all the boundaries.

For problems with a limited number of training samples such as biological expression data analysis, however, neither of the two approaches is particularly efficient in utilizing the information from the training data.

Therefore, there is a critical need for methods and systems that take advantages from both the traditional statistical approach and the empirical risk minimization approach, and provide a quantitative mechanism to incorporate prior knowledge into the data analysis process.

SUMMARY OF THE INVENTION

In one aspect, the present invention relates to a method for processing information in a data set that contains samples of at least two classes using an empirical risk minimization model, wherein each sample in the data set has an importance score. In one embodiment, the method includes the step of selecting samples of a first class being labeled with class label +1 and a second class with class label −1, from the data set, prescribing an empirical risk minimization model using the selected samples with an objective function and a plurality of constraints which adequately describes the solution of a classifier to separate the selected samples into the first class and the second class, modifying the empirical risk minimization model to include terms that individually limit the influence of each sample relative to its importance score in the solution of the empirical risk minimization model, and solving the modified empirical risk minimization model to obtain the corresponding classifier to separate the samples into the first class and the second class.

In another aspect, the present invention relates to a method for processing information in a data set of m samples $x_i$, i=1, 2, . . . , m with the corresponding class membership labels $c_i$, i=1, 2, . . . , m, $\epsilon\{-1, +1\}$. In the data set, each sample includes measurements of n variables. In one embodiment, the method for processing information includes the steps of assigning to each sample $x_i$ a relative importance score $p_i \geq 0$, $p_i$ representing the trustworthiness of sample $x_i$; minimizing $$\frac{1}{2}\upsilon \cdot \upsilon + \sum_{i=1}^{m} p_i \xi_i$$

subjecting to $c_i(\upsilon \cdot x_i+b) \geq 1-\xi_i$, i=1, 2, . . . , m to obtain a solution comprising $\upsilon$ and b, wherein $\xi_i$ represents a non-negative error for the ith constraint, and constructing an n-dimensional unit vector $d=v/\|v\|=(d_1 \ d_2 \ \ldots \ d_n)^T$ from the solution that identifies a direction along which the samples are best separated into a first class labeled as +1 and a second class labeled as −1, respectively, for the set of assigned importance scores $p_1, p_2, \ldots, p_m$.

The method for processing information in a data set, in a further embodiment, for a pair of parameters σ and C, includes a step of performing a backward stepwise variable selection procedure. The step of performing a backward stepwise variable selection procedure in turn includes the steps of (a) assigning each variable in the data set with an initial temporary significance score of zero, (b) computing a temporary significance score for each variable in the data set based on the absolute value of the corresponding element in $d=v/\|v\|$ from the solution and the variable's temporary significance score, (c) finding the variable in the data set with the smallest temporary significance score, (d) assigning the temporary significance score of the variable as its final significance score and removing it from the data set to be used in future iterations, (e) repeating steps (b)–(d) until all variables in the data set have been assigned a final significance score, and (f) constructing a vector $s=(s^1 \ s^2 \ \ldots \ s^n)$, wherein $s^k$, j=1, . . . , n, represents a computed final significance score for the kth variable of the n variables in the separation of the samples into the first and second classes.

The method for processing information in a data set, in yet a further embodiment, for a pair of parameters σ and C, includes a step of performing a component analysis procedure to determine q unit vectors, q≦min{m, n}, as projection vectors to a q dimensional component space. The step of performing a component analysis procedure in turn includes the following steps of (a) setting k=n, (b) obtaining unit vector $d=v/\|v\|$ from the solution using a current data set, (c) projecting the samples onto a (k−1) dimensional subspace perpendicular to the unit vector d and renaming these projections as the current data set, (d) saving d as a projection vector and setting k=k−1, and (e) repeating steps (b)–(d) until q projection vectors have been determined.

In yet another aspect, the present invention relates to a system for processing information in a data set having n variables and m samples $x_i$, i=1, 2, . . . , m with the corresponding class membership labels $c_i$, i=1, 2, . . . , m$\epsilon\{-1, +1\}$. The system includes an input device for receiving the information, and a processing unit communicating to the input device and performing the steps of assigning to each sample $x_i$ a relative importance score $p_i \geq 0$, $p_i$ representing the trustworthiness of sample $x_i$, minimizing $$\frac{1}{2}\upsilon \cdot \upsilon + \sum_{i=1}^{m} p_i \xi_i$$

subjecting to constraints of $c_i(\upsilon x_i+b) \geq 1-\xi_i$, i=1, 2, . . . , m to obtain a solution comprising $\upsilon$ and b, wherein $\xi_i$ represents a non-negative error for the ith constraint, and constructing an n-dimensional unit vector $d=v/|v|=(d_1 \ d_2 \ \ldots \ d_n)^T$ from the solution to identify a direction along which the samples are best separated into a first class labeled as +1 and a second class labeled as −1 for the set of assigned importance scores $p_1, p_2, \ldots p_m$.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

Figure 2:
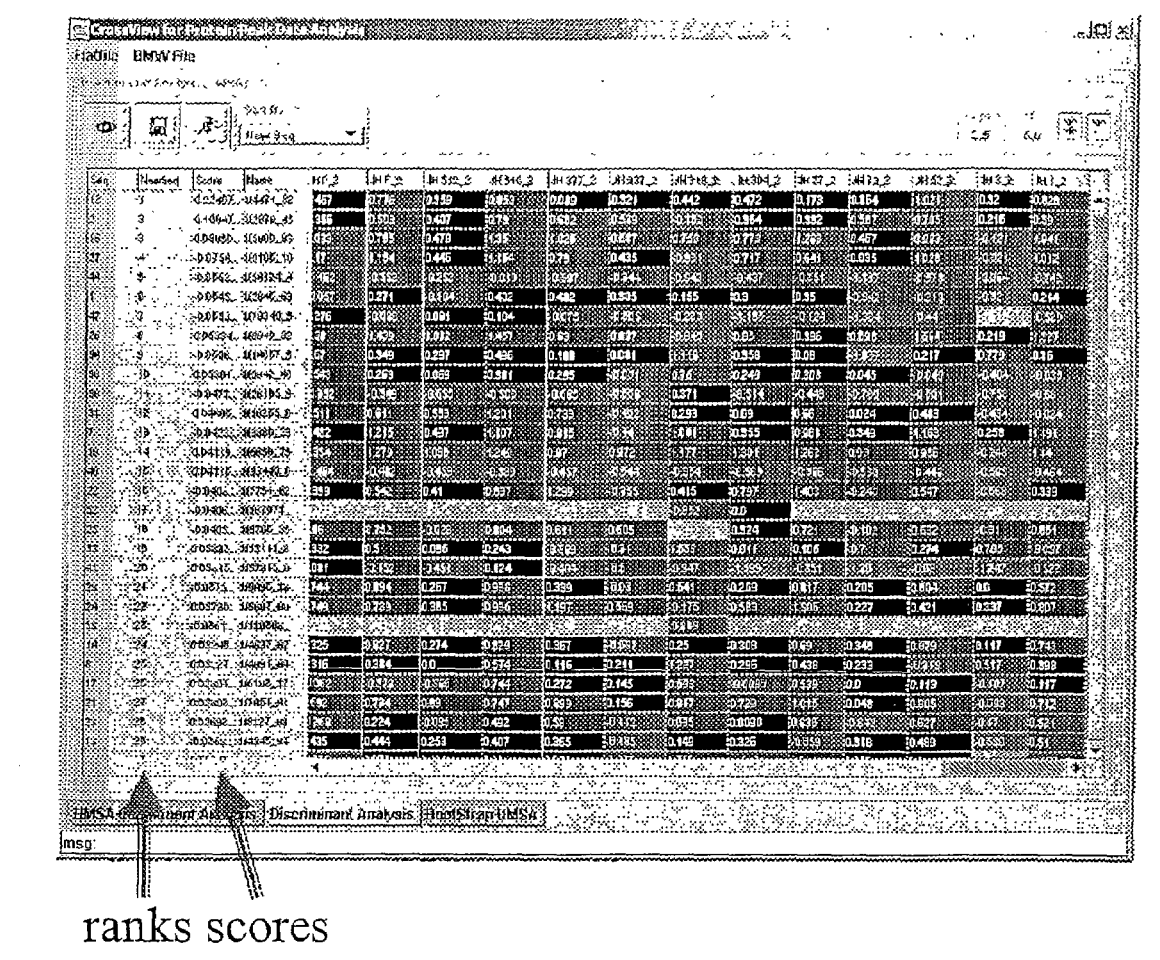

FIG. 2 is a snapshot of the user interface of the backward stepwise variable selection module according to one embodiment of the present invention.

DETAILED DESCRIPTION OF THE INVENTION

Figure 1:
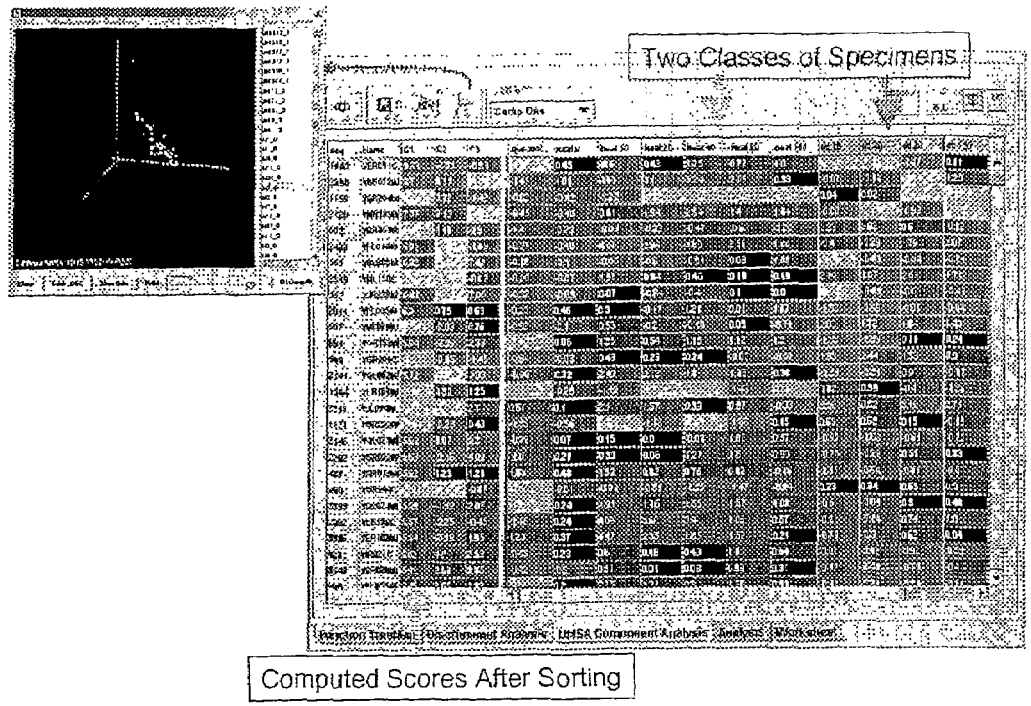
FIG. 1 is a snapshot of the user interface and 3-Dimensional ("3D") plot of a UMSA component module according to one embodiment of the present invention.

Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

In one aspect, referring in general to FIGS. 1–8, the present invention relates to a method for processing information in a data set that contains samples of at least two classes using an empirical risk minimization model, wherein each sample in the data set has an importance score. In one embodiment, the method includes the step of selecting samples of a first class being labeled with class label +1 and a second class with class label −1, from the data set, prescribing an empirical risk minimization model using the selected samples with an objective function and a plurality of constraints which adequately describes the solution of a classifier to separate the selected samples into the first class and the second class, modifying the empirical risk minimization model to include terms that individually limit the influence of each sample relative to its importance score in the solution of the empirical risk minimization model, and solving the modified empirical risk minimization model to obtain the corresponding classifier to separate the samples into the first class and the second class. As used in the description herein and throughout the claims that follow, the meaning of term "processing" includes collecting, selecting, classifying, analyzing, or any other act on data directly or indirectly by a human being or a man-made device such as a computer that is capable of interfacing with a human being. The assignment of the specific numerical values +1 as label to the first class of samples and −1 to the second class of samples is to simplify the mathematical expression of the abovementioned empirical risk minimization model with an objective function and a plurality of constraints. Other numerical assignment of labels of distinctive values can also be used and can be proved to be equivalent to the presentation used for the current invention even though the formulation will be in a more complex form.

Each sample includes measurements of expression levels of a plurality of selected known or unknown biological entities in a corresponding biological specimen. Moreover, the class of a sample as identified by class label +1 or −1, respectively, indicates the phenotype of the biological specimen comprising the presence, absence, or severity of a plurality of biological conditions or perturbations associated with the biological specimen, respectively. A biological entity may include a plurality of cellular constituents.

The importance score of a sample is a unitless number representing the relative trustworthiness of the sample. The method of the present invention further includes the step of obtaining an importance score for each sample from information related to the data set. In one embodiment, the step of obtaining an importance score for each sample from information related to the data set further includes the steps of deriving a statistical classification model using the data set, applying the classification model to a sample to generate an output, and comparing the output to the known class label of the sample to compute an importance score for the sample such that a sample that is misclassified or considered outliers based on the output of said classification model is assigned a relatively lower importance score.

The method for processing information in a data set, in yet another embodiment, further includes the steps of introducing a new sample x, applying the classifier on x and obtaining an output y, and assigning the sample x to the class corresponding to the label +1 or −1 based on a cutoff on y.

In an embodiment, the relative importance score is computed using training samples. The numerical function f(x) can be a linear or nonlinear statistical classifier constructed using the training samples based on parametric or non-parametric methods. The sign of the value f(x) classifies the sample x to the class labeled +1 or −1, respectively and the absolute value of f(x) reflects the confidence of such a classification. The importance score of a sample x in the training data will then be computed by a non-negative function $h(f(x), y, q_1, q_2, \ldots, q_r)$, where $y \in \{-1,+1\}$ is the class label of sample x, $q_1, q_2, \ldots, q_r$ are parameters of $h(\cdot)$.

In yet another embodiment, the function $h(\cdot)=\Phi(f(x), y, C, \delta)$, where $\Phi(\cdot)$ is a non-negative function, $y \in \{-1,+1\}$ is the class label of sample x, and C and $\delta$ are parameters of $\Phi(\cdot)$.

In yet another embodiment, the statistical classifier f(x) is a linear classifier based on parametric methods such as Fisher's Linear Discriminant Analysis (LDA) or a nonlinear classifier based on quadratic discriminant analysis (or Mahanalobis distance) or based on non-parametric methods such as radial basis function (RBF) artificial neural network.

In yet another embodiment, to compute the importance scores using the training sample data, the function $h(x)=\Phi(f(x), y, C, \delta)$, take the form:

$$\delta = \begin{cases} 0, & \text{if } \text{sign}(f(x)) = \text{sign}(y) \\ |f(x)| \end{cases}, \text{ and}$$

$$h(x) = C\exp(-\delta^2/\sigma^2),$$

where $\delta$ equals zero for a sample that is correctly classified by the statistical classifier and equals the absolute value of f(x) if it is misclassified. The higher is this value, the more likely this sample is an outlier and should be of less importance in the late step of empirical risk minimization for the derivation of a final classifier. In the above formula, C is a positive and finite constant parameter representing the cap on maximum influence of any training sample. $\sigma$ is positive parameter that modulate the effect of the statistical classifier on the computation of importance scores. For a very large $\sigma$, $h(x) \approx C$. The effect of the statistical classifier becomes negligible. When $\sigma$ relatively small in comparison to the computed $\delta$s for all samples, samples misclassified badly by the statistical classifier (i.e., a large $\delta$) will have low importance scores.

Finally, optionally, the importance scores are estimated or assigned based on the quality or other information of the samples. This can be optionally related to the confidence of a sample's classification, the quality of the experimental and analytical processes that generated the measurement data.

In another aspect, still referring in general to FIGS. 1–8, the present invention relates to a method for processing information in a data set of m samples $x_i$, $i=1, 2, \ldots, m$ with the corresponding class membership labels $c_i$, $i=1, 2, \ldots, m$, $\in \{-1, +1\}$. In the data set, each sample includes measurements of n variables. In one embodiment, the method for processing information includes the steps of assigning to each sample $x_i$ a relative importance score $p_i \geq 0$, and minimizing $$\frac{1}{2} v \cdot v + \sum_{i=1}^{m} p_i \xi_i$$

subjecting to $c_i(v \cdot x + b) \geq 1 - \xi_i$, $i=1, 2, \ldots, m$ to obtain a solution comprising v and b, wherein $\xi_i$ represents a non-negative error for the ith constraint, and constructing an n-dimensional unit vector $d=v/\|v\|=(d_1 \ d_2 \ \ldots \ d_n)^T$ from the solution that identifies a direction along which the samples are best separated into a first class labeled as +1 and a second class labeled as −1, respectively, for the set of assigned importance scores $p_1, p_2, \ldots, p_m$.

The above formulation is similar to that of the standard soft-margin classifier used in SVM with the exception that the errors $\xi_i$, $i=1, 2, \ldots, m$ are constrained by the individualized $p_i$, $i=1, 2, \ldots, m$ instead of a single constant as in soft-margin classifier or SVM. In the above constrained minimization problem, the objective function consists of two terms. The first term, $\frac{1}{2}v \cdot v$, is to minimize the structural complexity of the classifier, and the second term $$\sum_{i=1}^{m} p_i \xi_i$$

is to minimize the classification error due to overlapping training samples of the two classes. The above formulation of constrained minimization, other than the use of importance scores as individualized constraints on the maximum influence of individual samples, is the same as in soft-margin classifier and SVM.

The definition of $\xi_i$s in the above formulation is the same as in the soft-margin classifier and SVM. They are introduced into the objective function as "slack variables" to allow for a solution of the above minimization problem when the two classes of samples partially overlap. Solving the above minimization problem determines a vector $v$ and a scalar $b$. The vector $v$ is a linear combination of the training samples:

$$v = \sum_{i=1}^{m} c_i \alpha_i x_i, \text{ where } 0 \leq \alpha_i \leq p_i.$$

Similar to SVM, typically only a subset of the training samples have nonzero $\alpha_i$s and are referred to as support vectors. It is clear that in the present invention the influence of the ith sample is individually constrained by its own assigned importance score $p_i$. The scalar $b$ of the solution is used to form the linear classifier:

$$f(x) = sgn(x \cdot \sigma + b)$$

where $sgn(\cdot)$ is the signum function.

The vector $v$ indicates a direction in the original variable space along which the two classes of samples are best separated by the linear classifier determined from solving the above minimization problem. The unit vector $d$ is the normalized vector $v$. As such constructed, the absolute value of the kth element in the n-dimensional unit vector $d$, $|d_k|$, $k=1, 2, \ldots, n$, corresponds to a relative significance measure of the kth variable in the separation of the samples into the first and second classes. Moreover, the sign, which can be + (positive) or − (negative), of the kth elements in the n-dimensional unit vector $d$, sign $(d_k)$, $k=1, 2, \ldots, n$, indicates whether the corresponding kth variable is upper regulated or down regulated with respect to the data class labeled as +1.

As used in herein and in the following description, unless the context clearly indicates otherwise, each sample may comprise n measurements of expression levels of a plurality of selected known or unknown biological entities in a corresponding biological specimen. The kth variable hence comprises measurements of expression levels of the kth selected known or unknown biological entity across all samples in the data set. The class of a sample as identified by class label +1 or −1, respectively, indicates the phenotype of the biological specimen comprising the presence, absence, or severity of a plurality of biological conditions or perturbations associated with the biological specimen. A biological entity may include a plurality of cellular constituents. Moreover, a biological entity may include a gene, a protein, or a fragment of a protein.

As used in herein, the term "biological sample" is broadly defined to include any cell, tissue, organ or multicellular organism. A biological sample can be derived, for example, from cell or tissue cultures in vitro. Alternatively, a biological sample can also be derived from a living organism or from a population of single cell organisms.

The method for processing information in a data set, in yet another embodiment, further includes the steps of introducing a new sample $x=(x_1 x_2 \ldots x_n)^T$, computing a scalar value $$y = d \cdot x = \sum_{j=1}^{n} d_j x_j,$$

and assigning the sample $x$ to the class corresponding to the label +1 if $y > y_c$ and to the class corresponding to the label −1 if $y \leq y_c$, respectively, wherein $y_c$ is a scalar cutoff value on $y$.

The method for processing information in a data set, in a further embodiment, includes a step of performing a backward stepwise variable selection procedure:

Procedure: Stepwise backward variable selection for a two-class dataset with n variables and m samples
inputs:
    dataset X of n variables and m samples; and
    class labels $\{c_1, c_2, \ldots, c_m\}$, $c_i \in \{-1,+1\}$.
while k>1
    a. apply one of the embodiments described above to process information in X to obtain a solution vector $v$ (as defined in the embodiment);
    b. use $v$ to compute the contributions of individual variables in X to the separation of the two classes in X;
    c. identify variable r that has the smallest contribution;
    d. based on the contribution of variable r, compute and assign a significance score $w_r$ to variable r,
    e. deactivate variable r in X in future calculation; and
    f. k←k−1.
return w and the order in which variables are removed.
In the above algorithm, "←" indicates the assignment operator.

The method for processing information in a data set, in yet a further embodiment, includes a step of performing a component analysis procedure to determine q unit vectors, $q \leq \min\{m, n\}$, as projection vectors to a q dimensional component space:

Procedure: Component analysis for a two-class dataset with n variables and m samples
inputs:
    desired number of components $q \leq \min(m, n)$;
    dataset X of n variables and m samples; and
    class labels $\{c_1, c_2, \ldots, c_m\}$, $c_i \in \{-1,+1\}$.
initialization:
    component set D←{};
    k>1.
while k≤q 1. apply one of the embodiments described above to process information in X to obtain a solution vector v (as defined in the embodiment);
2. $d^k \leftarrow v/\|v\|$ and $D \leftarrow D \cup \{d^k\}$;
3. X←projection of X onto (n–k)-dimensional subspace perpependicular to $d^k$;
4. k←k+1.

return D.

Figure 6:
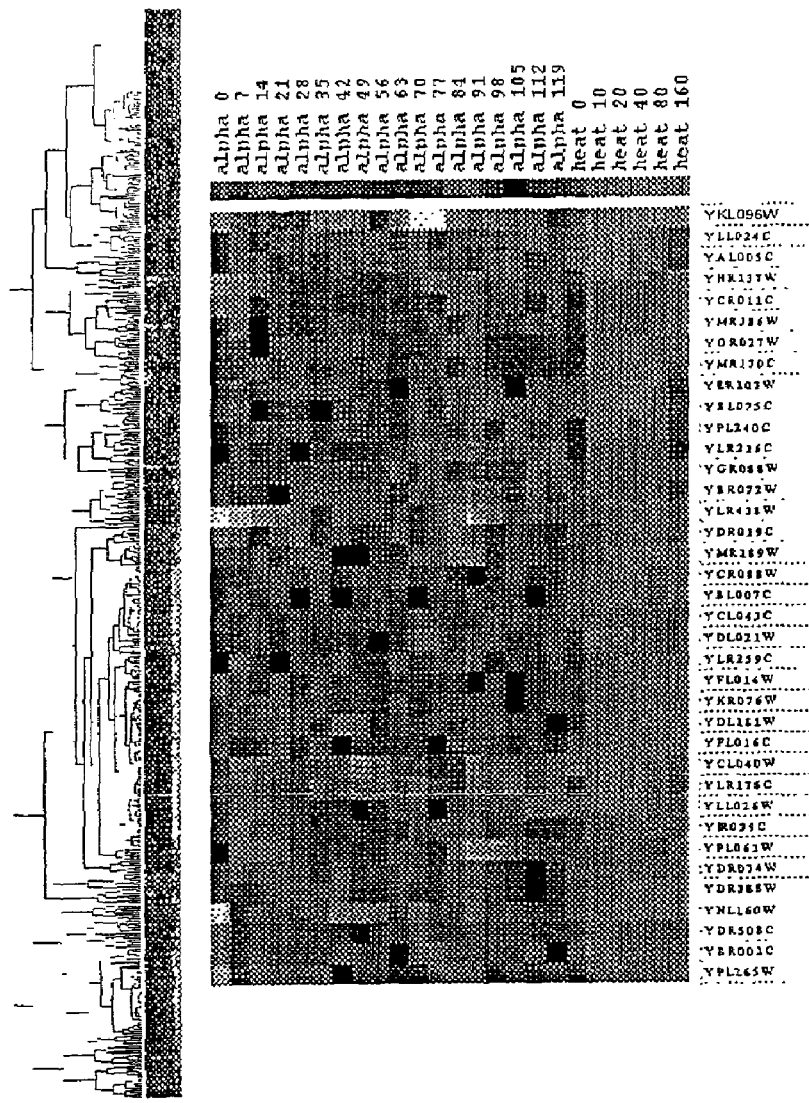
FIG. 6 shows a cluster of up-regulated genes under heat shock.
Figure 7:
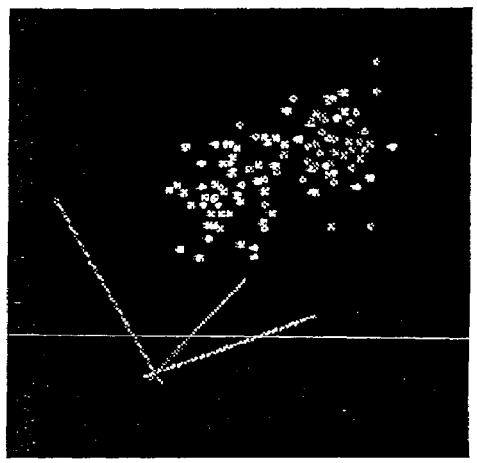
FIG. 7 illustrates (A) a 3D plot of samples from breast cancer patients and non-cancer women (including healthy control) in a UMSA component space, projected from an original 148 dimensional (peaks) space; and (B) a 3D plot of the same samples in a 3D space represented by three selected protein peaks as potential biomarkers. The selected peaks retain almost all separating power in the original 148 peaks.
Figure 7:
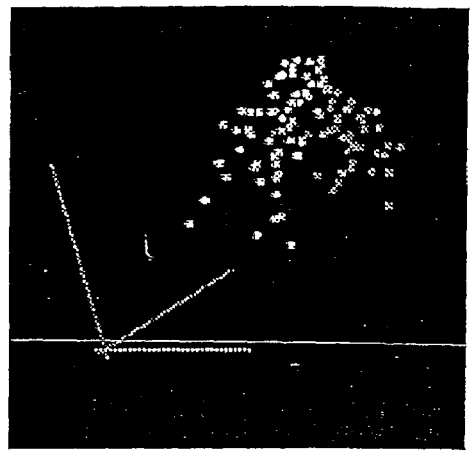
Figure 8:
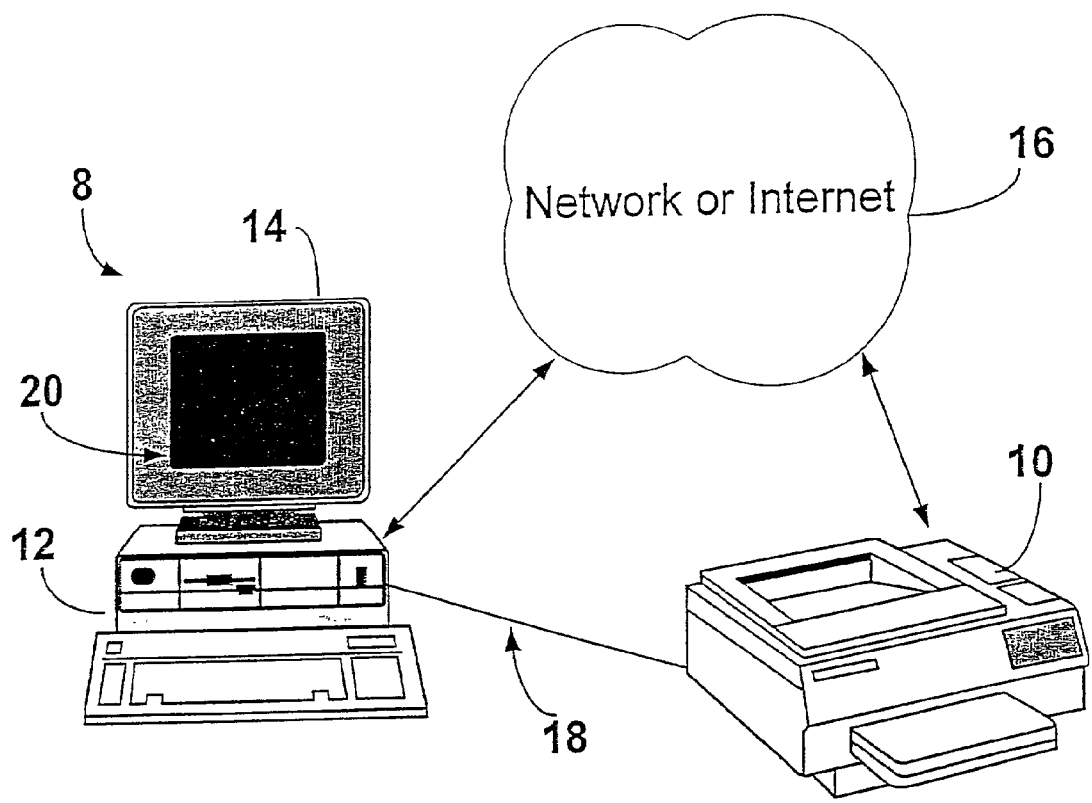
FIG. 8 shows a block-diagram of a system that can be utilized to practice the present invention.

In yet another aspect, still referring in general to FIGS. 1–8, in particular to FIG. 8, there is shown a perspective view of the inventive system 100 including a host computer 8 having a host processor 12 with a display 14, such as a monitor, having a graphic-user interface (GUI) 20 displaying data for at least one peripheral device 10. The peripheral device 10 can be an input device to receive data or out put device for output data, shown here as a printer, in operative communication with the host processor 12. The printer 10 and host processor 12 can be in communication through any media, such as a direct wire connection 18 or through a network or the Internet 16. Even wireless communication between the printer 10 and host processor 12 can be used with the present invention as long as data can be exchanged between the printer 10 and host processor 12. The GUI 20 is generated by a GUI code as part of the operating system (O/S) of the host processor 12. As those skilled in the art will appreciate, the data to be processed in the system 100 can be stored in a memory device (not shown) or can be, provided in the form of a computer readable medium. Examples of computer readable media include: recordable type media such as floppy disks and CD-ROMs and transmission type media such as digital and analog communication links. Likewise, the result of processed data can be displayed in GUI 20, printed by printer 10, saved in a memory device (not shown), transmitted over network 16 or can be, provided in the form of the computer readable medium.

In one embodiment, the present invention relates to a system for processing information in a data set having n variables and m samples $x_i$, i=1, 2, . . . , m with the corresponding class membership labels $c_i$, i=1, 2, . . . , m∈{–1, +1}. The system includes an input device for receiving the information, and a processing unit communicating to the input device and performing the steps of assigning to each sample $x_i$ a relative importance score $p_i \geq 0$, and minimizing $$\frac{1}{2} v \cdot v + \sum_{i=1}^{m} p_i \xi_i$$

subjecting to constraints of $c_i(v \cdot x_i + b) \geq 1 - \xi_i$, i=1, 2, . . . , m to obtain a solution comprising v and b, wherein $\xi_i$ represents a non-negative error for the ith constraint, and constructing an n-dimensional unit vector $d = v/\|v\| = (d_1\ d_2\ \ldots\ d_n)^T$ from the solution to identify a direction along which the samples are best separated into a first class labeled as +1 and a second class labeled as –1 for the set of assigned importance scores $p_1, p_2, p_m$.

The above formulation is similar to that of the standard soft-margin classifier used in SVM with the exception that the errors $\xi_i$, i=1, 2, . . . , m are constrained by the individualized $p_i$, i=1, 2, . . . , m instead of a single constant as in soft-margin classifier or SVM. In the above constrained minimization problem, the objective function includes two terms. The first term, $\frac{1}{2} v \cdot v$, is to minimize the structural complexity of the classifier, and the second term $$\sum_{i=1}^{m} p_i \xi_i$$

is to minimize the classification error due to overlapping training samples of the two classes. The above formulation of constrained minimization, other than the use of importance scores as individualized constraints on the maximum influence of individual samples, is the same as in soft-margin classifier and SVM.

The definition of $\xi_i$s in the above formulation is the same as in the soft-margin classifier and SVM. They are introduced into the objective function as "slack variables" (variables which are introduced when inequality constraints are replaced by equalities) to allow for a solution of the above minimization problem when the two classes of samples partially overlap. Solving the above minimization problem determines a vector v and a scalar b. The vector v is a linear combination of the training samples:

$$v = \sum_{i=1}^{m} c_i \alpha_i x_i, \text{ where } 0 \leq \alpha_i \leq p_i.$$

Similar to SVM, typically only a subset of the training samples have nonzero $\alpha_i$s and are referred to as support vectors. Accordingly, the influence of the ith sample can be individually constrained by its own assigned importance score $p_i$. The scalar b of the solution is used to form the linear classifier:

$$f(x) = sgn(x \cdot v + b)$$

where sgn(·) is the signum function.

The vector v can indicate a direction in the original variable space along which the two classes of samples are best separated by the linear classifier determined from solving the above minimization problem. The unit vector d is the normalized vector v.

The processing unit may comprise a microprocessor such as host processor 12. The input device may include a microprocessor interface. The input device further may include at least one device selected from the group of a GUI, a scanner, a CD-ROM, a diskette, a computer coupled to a network, a networking device, any combination of them, or the like. Additionally, the system may further include an output device coupled to the processing unit, wherein the output device comprises at least one device selected from the group of a GUI, a printer, a CD-ROM, a diskette, a computer coupled to a network, a networking device, any combination of them, or the like.

In a further aspect, the present invention relates to a unified maximum separability analysis ("UMSA") algorithm as partially defined below:

A UMSA classifier for a set of m training samples $x_1, x_2, \ldots, x_m$ drawn from distributions $D^+$ and $D^-$ with the corresponding class membership labels $c_1, c_2, \ldots, c_m \in \{-1, +1\}$ is determined by solving the following constrained optimization problem:

Minimize $$\frac{1}{2} v \cdot v + \sum_{i=1}^{m} p_i \xi_i \qquad \text{[equation 1]}$$

subject to $c_i(v \cdot x_i + b) \geq 1 - \xi_i$, $i=1, 2, \ldots, m$, where the non-negative variables $\xi_1, \xi_2, \ldots, \xi_m$ represent errors in the constraints that are penalized in the object function, and the coefficients $p_1, p_2, \ldots, p_m$ are positive constants reflecting the relative "importance" of the individual samples.

In the second term in equation 1, if the individual importance scores, $p_1 = p_2 = \ldots = p_m = C$, are the same constant for all m training samples, the UMSA classification model becomes the optimal soft-margin hyperplane classification model as commonly used in the so-called Support Vector Machine classification models. In deriving the optimal soft-margin hyperplane classification model, the constant C in the second term of equation 1 defines the maximum influence ANY misclassified sample may have on the overall optimization process. The resultant classification model is determined (supported) by only those training samples that are close to the classification boundary and are hence called support vectors.

In the present invention, the UMSA algorithm introduces the concept of relative importance scores that are individualized for each training sample. Through this mechanism, prior knowledge about the individual training samples may be incorporated into the optimization process. The resultant classification model will be preferentially influenced more by the "important" samples.

Optionally, the individualized importance scores may be computed based on properties estimated from the training samples so that $p_i = \phi(x_i, D^+, D^-) > 0$.

Optionally, the function $p_i = \Phi(f(x), y, C, \delta)$, where $\Phi(\cdot)$ is a non-negative function, $f(x)$ is a a linear or nonlinear statistical classifier constructed using the training samples drawn from $D^+$ and $D^-$ based on parametric or non-parametric methods. The sign of the value $f(x)$ classifies the sample x to the class labeled +1 or −1, respectively and the absolute value of $f(x)$ reflects the confidence of such a classification. $y \in \{-1, +1\}$ is the class label of sample x, and C and $\epsilon$ are parameters of $\Phi(\cdot)$.

Yet further optionally, the statistical classifier $f(x)$ is a linear classifier based on parametric methods such as Fisher's Linear Discriminant Analysis (LDA) or a nonlinear classifier based on quadratic discriminant analysis (or Mahanalobis distance) or based on non-parametric methods such as radial basis function (RBF) artificial neural network.

Furthermore, the importance score $p_i$ may be optionally defined to be inversely related to the level of disagreement of a sample $x_i$ to a classifier derived based on training samples drawn from the distributions $D^+$ and $D^-$. Let this level of disagreement be $\delta_i$, the following positive decreasing function may be optionally used to compute $p_i$:

$$p_i = C \cdot e^{-\delta_i/\sigma^2}, \qquad \text{[Equation 2]}$$

where C is a positive and finite number. $\sigma$ is a positive number.

In equation 2, the parameter C limits the maximum influence a misclassified training sample may have in the overall optimization process. The parameter a modulates the influence of individual training samples. A very large $\sigma$ will cause equation 2 to be essentially a constant. The UMSA classification model becomes a regular optimal soft-margin hyperplane classification model. On the other hand, a small $\sigma$ amplifies the effect of $\delta_i$.

As a specially case, the level of disagreement of a sample $x_i$ to a classifier derived based on training samples drawn from the distributions $D^+$ and $D^-$ may be optionally computed as $$\delta = \begin{cases} 0, & \text{if } \text{sign}(f(x)) = \text{sign}(y) \\ |f(x)| \end{cases}, \text{ and}$$

As a special case for expression data with very few samples and an extremely large number of variables, which make the direct estimation of conditional distributions difficult, the level of disagreement $\delta_i$ may be optionally defined as the shortest distance between the data point $x_i$ and the line that goes through the two class means.

The UMSA derived classification model is both determined by training samples close to the classification boundaries (support vectors) and influenced by additional information from prior knowledge or data distributions estimated from training samples. It is a hybrid of the traditional approach of deriving classification model based on estimated conditional distributions and the pure empirical risk minimization approach. For biological expression data with a small sample size, UMSA's efficient use of information offers an important advantage. This efficient use of information also makes the results less sensitive to errors in sample class labels. For biological expression data, such sample labeling errors can be quite common due to misdiagnosis of patients or sample contamination in specimen collection procedures such as tissue dissection.

In yet another aspect, the present invention can be utilized to provide following two analytical modules: A) a UMSA component analysis module; and B) a backward stepwise variable selection module, as discussed above and below.

UMSA component analysis. The basic algorithm iteratively computes a projection vector d along which two classes of data are optimally separated for a given set of UMSA parameters. The data are then projected onto a subspace perpendicular to d. In the next iteration, UMSA is applied to compute a new projection vector within this subspace. The iteration continues until a desired number of components have been reached. For interactive 3D data visualization, often only three components are needed. Depending on the shape of data distribution, for many practical problems, three dimensions appear to be sufficient to "extract" all the significant linear separation between two classes of data. The following is a component analysis algorithm for a data set of m samples and n variables:

Procedure: UMSA Component analysis for a two-class dataset with n variables and m samples inputs:
1. desired number of components $q \leq \min(m, n)$;
2. user specified UMSA parameters C and $\sigma$,
3. dataset $X = \{x_i | j=1, 2, \ldots, m\}$ of m samples, where a sample $x_i = (x_{i1}, x_{i2}, \ldots, x_{in})^\tau$ is represented by an n element vector;
4. class labels $\{c_1, c_2, \ldots, c_m\}$, $c_i \in \{-1, +1\}$; and 5. a prescribed procedure to be used in UMSA to construct a statistical classifier using the given training samples and to compute the importance score for individual samples.

initialization:
1. k←1;
2. component set D←{};

while k≤q
1. applying UMSA on X and the class labels to obtain the solution vector v, (as defined in UMSA);
2. $d^k \leftarrow v/\|v\|$ and $D \leftarrow D \cup \{d^k\}$;
3. X←projection of X onto (n-k)-dimensional subspace perpendicular to $d^k$ (one way to implement: for all samples in X, $x_i \leftarrow x_i - (x_i^\tau d^k) d^k$, i=1,2, ..., m);
4. k←k+1.

return D.

In the above algorithm, "←" indicates the assignment operator.

Additionally, the UMSA component analysis method is similar to the commonly used principal component method (PCA) or Singular Value Decomposition (SVD) in that they all reduce data dimension. The difference is that in PCA/SVD, the components represent directions along which the data have maximum variations while in UMSA component analysis, the components correspond to directions along which two predefined classes of data achieve maximum separation. Thus, while PCA/SVD are for data representation, UMSA Component Analysis is for data classification (this is also why in many cases, a three dimensional component space is sufficient for linear classification analysis).

Backward stepwise variable selection module. For a biological expression data set formulated as an n variables x m samples matrix X, this module is implemented in the algorithm below. The returned vector w contains the computed significance scores of the n variables in separating the two predefined classes of samples:

Procedure: UMSA Stepwise backward variable selection for a two-class dataset with n variables and m samples
6. user specified UMSA parameters C and σ,
7. dataset X={$x_i$|j=1,2, ..., m} of m samples, where a sample $x_i = (x_{i1}, x_{i2}, \ldots, x_{in})^\tau$ is represented by an n element vector;
8. class labels {$c_1, c_2, \ldots, c_m$}, $c_i \in \{-1, +1\}$; and
9. a prescribed procedure to be used in UMSA to construct a statistical classifier using the given training samples and to compute the importance score for individual samples.

initialization:
1. k←n;
2. significance score vector $w = (w_1, w_2, \ldots, w_n)^\tau \leftarrow (0, 0, \ldots, 0)^\tau$.

while k>1
5. applying UMSA on X and the class labels to obtain the solution vector v (as defined in UMSA);
6. $s \leftarrow 2/\|v\|$ and $d \leftarrow \theta/\|v\|$;
7. for variable j in X, if $s|d_j| > w_j \leftarrow s|d_j|$; and
8. deactivate variable r in X in future calculation, where r is determined from $$w_r = \min_{\text{all active variables in } X_k} \{w_j\}; \text{ and}$$

9. k←k-1.

return w and the order in which variables are deactivated.

In the above algorithm, "←" indicates the assignment operator.

FIG. 7 show snapshots of A) the user interface of the UMSA component analysis module and B) the backward stepwise variable selection module as described above, respectively. The present invention has been successfully utilized to provide several embodiment examples as shown below.

A first dataset from the budding yeast saccharomyces cerevisiae (Eisen 1998) was used to demonstrate the backward stepwise variable selection module. A second data set, a protein profiling data set for tumor marker discovery for breast cancer, was generated using the Surface-Enhanced Laser Desorption/Ionization (SELDI) technology with the ProteinChip array manufactured by Ciphergen (Fremont, Calif.) (Li 2002). The original Data was mass spectra. Using manufacturer's software, significant mass peaks were detected. After appropriate normalization and other preprocessing steps as known to people skilled in the art, the data was formulated as an n peaks x m sample matrix. The kth entry of the ith column of the matrix represents the intensity of the kth peak (or the relative abundance of the corresponding protein) from the ith patient specimen. The UMSA component analysis module was used to project the data onto a 3-dimensional space for visualization of the separation of specimens from patients in different diagnostic groups.

Figure 3:
FIG. 3 shows the cluster analysis result of yeast genes after being ranked and sorted in groups of five hundred each.
Figure 3:
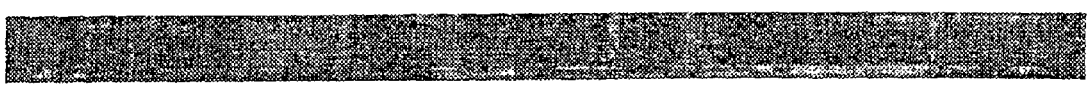
Figure 3:
Figure 3:

In application, for the yeast dataset, the endpoint of interest was chosen to be the identification of genes that are responsive to heat shock. The ranking and selection of genes were based on their contribution to the separation of arrays of specimens from cells in normal division cycles and those under heat shock at various time points (excluding time 0 since no change has between in effect). After the genes were ranked and sorted, hierarchical cluster analysis (Eisen, 1998) was applied to the genes, five hundred at a time, to displace the expression patterns of genes. FIG. 3 shows the results. As shown, it is clear that the first five hundred selected genes demonstrated clear patterns in gene expression levels that separate yeast cell in normal division cycles and those under heat shock. On the other hand the last five hundred genes with the least contribution to separation show almost total random patterns even after the cluster analysis. This demonstrated the effectiveness of the method described in the present invention.

Figure 4:
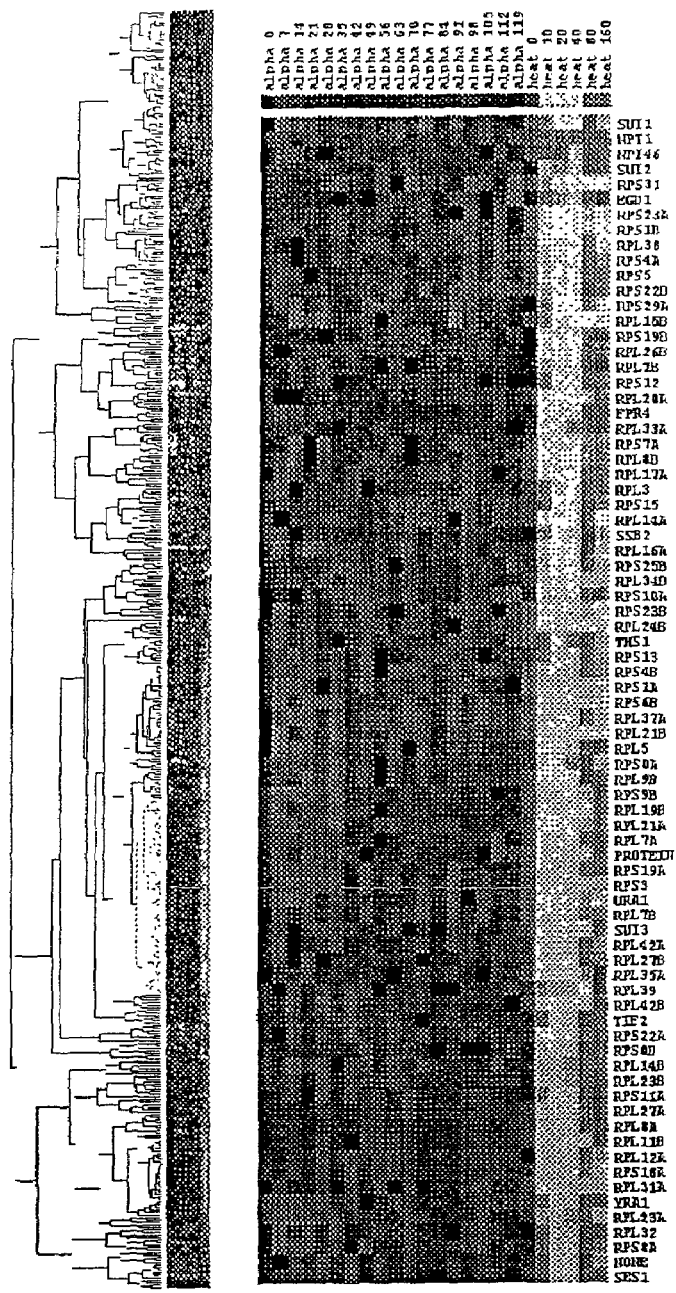
FIG. 4 shows a cluster of down-regulated genes under heat shock.
Figure 5:
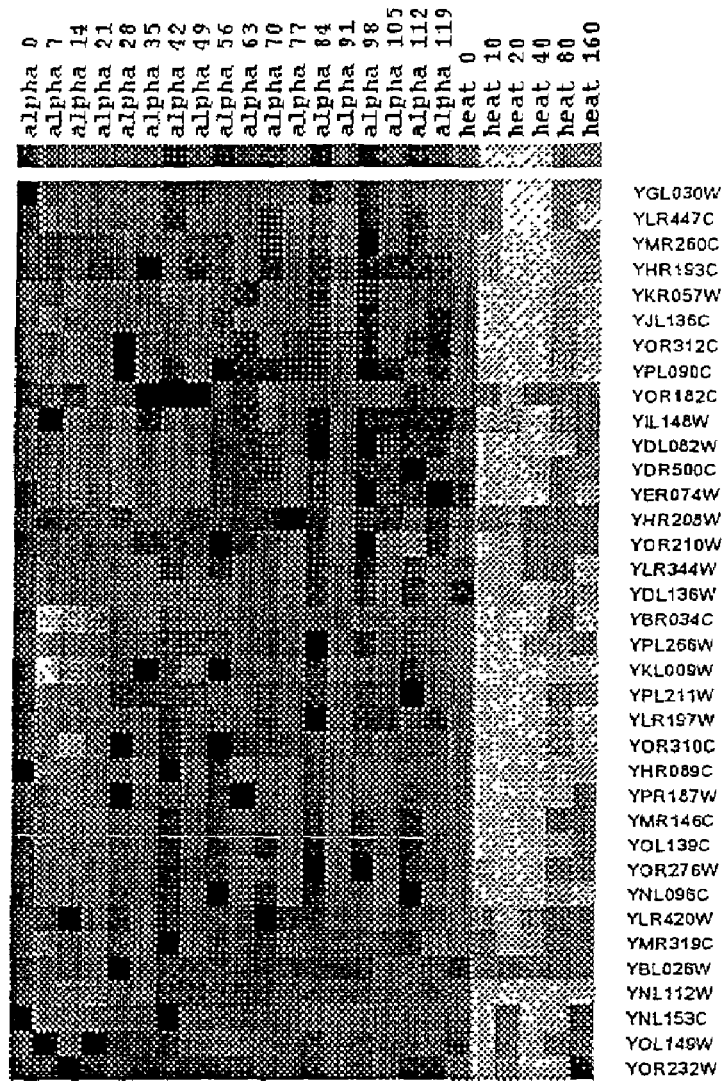
FIG. 5 shows another cluster of down-regulated genes under heat shock.

Furthermore, in FIGS. 4–6, some of these genes are displayed in detail. These results are biologically plausible and are consistent with results from other researchers such as (Gasch et. al, 2000). The down regulated clusters are composed primarily of ribosomal proteins, as expected since protein synthesis is strongly down regulated in heat shock conditions (regulated by transcription factor Rap1p), and genes involved in RNA metabolism. The clusters of strongly up regulated genes appear to have two classes of genes: the class of heat shock proteins, chaperoning, and other genes involved in cellular and protein stability; and the class of genes involved in metabolism and the uptake of metabolites. In response to heat shock, the cells are not making many new proteins, and at the same time are trying to protect the existing proteins and to expand the list of possible energy sources.

For the analysis of breast cancer data from protein profiling, FIG. 7 (A) shows the projection of the cancer and non-cancer samples onto a 3D UMSA component space from the original 148 (peaks) dimensional space. FIG. 7 (B) shows the same samples projected in a space represented by only the three most significant peaks selected using the backward stepwise variable selection module and validated through bootstrap methods. It shows that the three selected peaks retain most of the separating power of the original 148 peaks.

All references cited herein are incorporated herein by reference in their entirety and for all purposes to the same extent as if each individual publication or patent or patent application was specifically and individually indicated to be incorporated by reference in its entirety for all purposes.

While there has been shown various embodiments of the present invention, it is to be understood that certain changes can be made in the form and arrangement of the elements of the system and steps of the method(s) as would be known to one skilled in the art without departing from the underlying scope of the invention as is particularly set forth in the Claims. Furthermore, the embodiments described above are only intended to illustrate the principles of the present invention and are not intended to limit the claims to the disclosed elements.

REFERENCES

Fisher, A. (1923) The Mathematical Theory of Probabilities, Vol. 1, (Macmillan, New York).
Cortes, C, and Vapnik, V. N. Support vector networks. Machine Learning, 20:273–297, (1995)
Eisen, M B, Spellman P, Brown P O and Botstein D, Proc Natl. Acad. Sci. 95, 14863–14868. (1998).
Vapnik, V. N. (1998) Statistical Learning Theory, (John Wiley & Sons, New York), pp. 401–441.
Perou C M et. al Proc Natl. Acad. Sci. 96, 9212–9217. (1999).
Lockhart D J and Winzeler E A, Nature, 405, 827–836. (2000).
Gasch A P, Spellman P T, Kao C M, Carmel-Harel O, Eisen M B, Storz G, Botstein D, Brown P O, Genomic Expression Programs in the Response of Yeast Cells to Environmental Changes, Mol Biol Cell 11(12):4241–4257. (2000).
Alter O, Brown P O, and Bostein D, Proc Natl. Acad. Sci. 97, 10101–10106. (2000).
Li J et. al Clinical Chemistry, in press (2002).

What is claimed is:

1. A method for processing information in a data set that contains samples of at least two classes using an empirical risk minimization model, wherein each sample in the data set has an importance score, comprising:
   a. selecting samples of a first class being labeled with class label +1 and a second class with class label −1, from the data set;
   b. prescribing an empirical risk minimization problem associated with a classifier model using the selected samples, wherein the empirical risk minimization problem has a plurality of constraints and an objective function which consists of an empirical risk function related to the classification errors of the selected samples by the associated classifier model and an additional term related to the complexity of the classifier model, and the solution of the empirical risk minimization problem adequately defines a classifier to separate the selected samples into the first class and the second class;
   c. modifying the empirical risk minimization model to include sample-specific importance scores that individually limit the influence of each sample in the solution of the empirical risk minimization problem; and
   d. solving the modified empirical risk minimization problem to obtain the corresponding classifier to separate the samples into the first class and the second class.

2. The method of claim 1, wherein each sample comprises measurements of expression levels of a plurality of selected known or unknown biological entities in a corresponding biological specimen.

3. The method of claim 2, wherein the class of a sample as identified by class label +1 or −1, respectively, indicates the phenotype of the biological specimen comprising the presence, absence, or severity of a plurality of biological conditions or perturbations associated with the biological specimen, respectively.

4. The method of claim 2, wherein a biological entity comprises a plurality of cellular constituents.

5. The method of claim 1, wherein the importance score of a sample represents the relative trustworthiness of the sample.

6. The method of claim 5, further comprising the step of obtaining an importance score for each sample from information related to the data set.

7. The method of claim 6, wherein the step of obtaining an importance score for each sample from information related to the data set further comprising the steps of:
   a. deriving a statistical classification model using the data set;
   b. applying the classification model to a sample to generate an output; and
   c. comparing the output to the known class label of the sample to compute an importance score for the sample such that a sample that is misclassified or considered outliers based on the output of said classification model is assigned a relatively lower importance score.

8. The method of claim 1, further comprising the steps of:
   a. introducing a new sample x;
   b. applying the classifier on x and obtaining an output y; and
   c. assigning the sample x to the class corresponding to the label +1 or −1 based on a cutoff on y.

9. A method for processing information in a data set of m samples $x_i$, i=1, 2, . . . , m with the corresponding class membership labels $c_i$, i=1, 2, . . . , m, $\in \{-1, +1\}$, each sample comprising measurements of n variables, comprising:
   a. assigning to each sample $x_i$ a relative importance score $p_i \geq 0$;
   b. minimizing $$y = d \cdot x = \sum_{j=1}^{n} d_j x_j,$$

subjecting to $c_i(v \cdot x + b) \geq 1 - \xi_i$, i=1, 2, . . . , m
   to obtain a solution comprising v and b, wherein $\xi_i$ represents a non-negative error for the ith constraint; and
   c. constructing an n-dimensional unit vector $d = v/\|v\| = (d_1 \, d_2 \, \ldots \, d_n)^T$ from the solution that identifies a direction along which the samples are best separated into a first class labeled as +1 and a second class labeled as −1, respectively, for the set of assigned importance scores $p_1, p_2, \ldots, p_m$.

10. The method of claim 8, wherein the absolute value of the kth element in the n-dimensional unit vector d, $|d_k|$, k=1, 2, ..., n, corresponds to a relative significance measure of the kth variable in the separation of the samples into the first and second classes.

11. The method of claim 8, wherein the sign of the kth elements in the n-dimensional unit vector d, $\text{sign}(d_k)$, k=1, 2, ..., n, indicates whether the corresponding kth variable is upper regulated or down regulated with respect to the data class labeled as +1.

12. The method of claim 9, 10 or 11, wherein each sample comprises n measurements of expression levels of a plurality of selected known or unknown biological entities in a corresponding biological specimen.

13. The method of 10 or 11, wherein the kth variable comprises measurements of expression levels of the kth selected known or unknown biological entity across all samples in the data set.

14. The method of claim 9, 10 or 11, wherein the class of a sample as identified by class label +1 or −1, respectively, indicates the phenotype of the biological specimen comprising the presence, absence, or severity of a plurality of biological conditions or perturbations associated with the biological specimen.

15. The method of claim 12, wherein a biological entity comprises a plurality of cellular constituents.

16. The method of claim 12, wherein a biological entity comprising a gene, a protein, or a fragment of a protein.

17. The method of claim 9, further comprising the steps of:
a. introducing a new sample $x=(x_1\ x_2\ \ldots\ x_n)^T$;
b. computing a scalar value $$\frac{1}{2}v \cdot v + \sum_{i=1}^{m} p_i \xi_i$$

and
c. assigning the sample x to the class corresponding to the label +1 if $y>y_c$ and to the class corresponding to the label −1 if $y \leq y_c$, respectively, wherein $y_c$ is a scalar cutoff value on y.

18. The method of claim 9, further comprising the steps of:
a. selecting a pair of constant positive values for parameter $\sigma$ and parameter C, respectively;
b. selecting a positive function $h(f(x), y, q_1, q_2, \ldots q_r)$, where f(x) is a linear or nonlinear statistical classifier constructed using the selected samples based on parametric or non-parametric methods, $y \in \{-1,+1\}$ is the class label of sample x, $q_1, q_2, \ldots q_r$ are parameters of $h(\cdot)$;
c. choosing the set of assigned importance scores $p_1, p_2, \ldots p_m$ in the form of $p_i=h(f(x_i), y_i, q_1, q_2, \ldots, q_r)$, i=1, ..., m; and
d. minimizing $$\frac{1}{2}v \cdot v + \sum_{i=1}^{m} p_i \xi_i$$

subjecting to constraints of $c_i(v \cdot x+b) \geq 1-\xi_i$, i=1, 2, ..., m to obtain a solution comprising v, wherein $\xi_i$ represents a non-negative error for the ith constraint.

19. The method of claim 18, wherein
for step b, the function has the form $h(x)=\Phi f(x), y, C, \delta)$ and the function f(x) is a linear classifier based on parametric methods such as Fisher's Linear Discriminant Analysis (LDA) or a nonlinear classifier based on quadratic discriminant analysis (or Mahanalobis distance) or based on non-parametric methods such as radial basis function (RBF) artificial neural network; and
step c further comprising:
computing a $\delta_i$ for each sample $x_i$, i=1, ..., m, $\delta_i$ being a quantitative measure of discrepancy between $x_i$'s known class label y and the output of f(x);
the importance score $p_i=h(f(x_i), y_i, C, \delta)$, i=1, ..., m.

20. The method of claim 19, wherein the importance score $p_i=C \cdot \exp(-\delta_i^2/\sigma^2)$, i=1, ..., m.

21. The method of claim 18, further comprising:
a. introducing a new sample $x=(x_1\ x_2\ \ldots\ x_n)^T$;
b. computing a scalar value $$y = d \cdot x = \sum_{j=1}^{n} d_j x_j;$$

and
c. assigning the sample x to the class corresponding to the label +1 if $y>y_c$ and to the class corresponding to the label −1 if $y \leq y_c$, respectively, where $y_c$ being a scalar cutoff value on y.

22. The method of claim 18, for a pair of $\sigma$ and C, and for a given data set X of m samples and n variables and the class labels of the m samples, further comprising a step of performing a backward stepwise variable selection procedure which comprises the steps of:
a. applying steps a–d of the method of claim 18 to process information in the current data set to obtain a solution vector v;
b. using v to compute the contributions of individual variables to the separation of the first class and the second class;
c. identify a variable r that has the smallest contribution;
d. based on the contribution of variable r, computing and assigning a significance score $w_r$ to variable r such that $w_r \geq$ significance scores of variables deactivated earlier,
e. deactivating variable r from future calculation; and
f. if the number of active variables in the data set >1, repeating from step a, else, returning the vector $\{w_i$, i=1, 2, ... n$\}$ which represents the computed significance scores to be used for variable selection.

23. The method of claim 22, wherein each sample comprises n measurements of expression levels of a plurality of selected known or unknown biological entities in a corresponding biological specimen.

24. The method of claim 22, wherein the kth variable comprises measurements of expression levels of the kth selected known or unknown biological entity across all samples in the data set.

25. The method of claim 22, wherein the class of a sample identified by class label +1 or −1, respectively, indicates the phenotype of the biological specimen comprising the presence, absence, or severity of a plurality of biological conditions or perturbations associated with the biological specimen, respectively.

26. The method of claim 23 or 24, wherein a biological entity comprises a plurality of cellular constituents.

27. The method of claim 23 or 24, wherein a biological entity comprising a gene, a protein, or a fragment of a protein.

28. The method of claim 18, for a pair of σ and C, and for a given data set X of m samples and n variables and the class labels of the m samples, further comprising a step of performing a component analysis procedure to determine q unit vectors, $q \leq \min\{m, n\}$, as projection vectors to a q dimensional component space, wherein the performing step comprises the following steps of:
   a. initializing component set $D \leftarrow \{\ \}$;
   b. applying steps a–d of the method of claim 18 to process information in the current data set to obtain a solution vector v;
   c. computing a unit projection vector $d^k \leftarrow v/\|v\|$ for the new component and adding it to the component set $D \leftarrow D \cup \{d^k\}$; and
   d. if the number of components in D=q, stopping and returning D, and if the number of components in D≠q, projecting the current data onto a subspace perpendicular to the unit projection vector $d^k$ of the newly computed component and repeating from step b.

29. The method of claim 28, wherein each sample comprises n measurements of expression levels of a plurality of selected known or unknown biological entities in a corresponding biological specimen.

30. The method of claim 28, wherein the kth variable comprises measurements of expression levels of the kth selected known or unknown biological entity across all samples in the data set.

31. The method of claim 28, wherein the class of a sample identified by class label +1 or −1, respectively, indicates the phenotype of the biological specimen comprising the presence, or absence, or severity of a plurality of biological conditions or perturbations associated with the biological specimen, respectively.

32. The method of claim 29 or 30, wherein a biological entity comprises a plurality of cellular constituents.

33. The method of claim 29 or 30, wherein a biological entity comprises a gene, a protein, a fragment of a protein.

34. A system for processing information in a data set having n variables and m samples $x_i$, i=1, 2, ..., m with the corresponding class labels $c_i$, i=1, 2, ..., m∈{−1, +1}, comprising:
   a. an input device for receiving the information; and
   b. a processing unit communicating to the input device and performing the steps of:
      i. assigning to each sample $x_i$ a relative importance score $p_i \geq 0$
      ii. minimizing $$\frac{1}{2} v \cdot v + \sum_{i=1}^{m} p_i \xi_i$$

subjecting to constraints of $c_i(v \cdot x + b) \geq 1 - \xi_i$, i=1, 2, ..., m to obtain a solution comprising v and b, wherein $\xi_i$ represents a non-negative error for the ith constraint; and
      iii. constructing an n-dimensional unit vector $d = v/\|v\| = (d_1\ d_2\ \ldots\ d_n)^T$ from the solution to identify a direction along which the samples are best separated into a first class labeled as +1 and a second class labeled as −1 for the set of assigned importance scores $p_1, p_2, \ldots, p_m$.

35. The system of claim 34, wherein the absolute value of the kth element in the n-dimensional unit vector d, $|d_k|$, k=1, 2, ..., n, corresponds to a relative significance measure of the kth variable in the separation of the samples into the first and second classes.

36. The system of claim 34, wherein the sign of the kth elements in the n-dimensional unit vector d, $\text{sign}(d_k)$, k=1, 2, ..., n, indicates whether the corresponding kth variable is upper regulated or down regulated with respect to the data class labeled as +1.

37. The system of claim 34, 35 or 36, wherein each sample comprises n measurements of expression levels of a plurality of selected known or unknown biological entities in a corresponding biological specimen.

38. The system of claim 35 or 36, wherein the kth variable comprises measurements of expression levels of the kth selected known or unknown biological entity across all samples in the data set.

39. The system of claim 34, 35 or 36, wherein the class of a sample identified by class label +1 or −1, respectively indicates the phenotype of the biological specimen comprising the presence, absence, or severity of a plurality of biological conditions or perturbations associated with the biological specimen, respectively.

40. The system of claim 37, wherein a biological entity comprises a plurality of cellular constituents.

41. The system of claim 37, wherein a biological entity comprises a gene or a protein or a fragment of a protein.

42. The system of claim 34, further comprising:
   a. introducing a new sample $x = (x_1\ x_2\ \ldots\ x_n)^T$;
   b. computing a scalar value $$y = d \cdot x = \sum_{j=i}^{n} d_j x_j;$$

and
   c. assigning the sample x to the class corresponding to the class label +1 if $y > y_c$ and to the class corresponding to the class label −1 if $y \leq y_c$, respectively, where $y_c$ is a scalar cutoff value on y.

43. The system of claim 34, wherein the processing unit comprises a microprocessor.

44. The system of claim 34, wherein the input device comprises a microprocessor interface.

45. The system of claim 34, wherein the input device further comprises at least one device selected from the group of a GUI, a scanner, a CD-ROM, a diskette, a computer coupled to a network, and a networking device.

46. The system of claim 34, further comprising an output device coupled to the processing unit.

47. The system of claim 34, wherein the output device comprises at least one device selected from the group of a GUI, a printer, a CD-ROM, a diskette, a computer coupled to a network, and a networking device.

* * * * *